United States Patent [19]

Gisel et al.

[11] Patent Number: 5,000,563
[45] Date of Patent: Mar. 19, 1991

[54] APPARATUS FOR OBSERVATION AND/OR TREATMENT OF A SEATED OR RECUMBENT PATIENT

[75] Inventors: Heinz Gisel, Horgen; Paul Bätscher, Munsingen, both of Switzerland

[73] Assignee: Lasag AG, Thun, Switzerland

[21] Appl. No.: 417,253

[22] Filed: Oct. 5, 1989

[30] Foreign Application Priority Data

Oct. 6, 1988 [CH] Switzerland ............. 03747/88

[51] Int. Cl.⁵ .................................. A61B 3/02
[52] U.S. Cl. .............................. 351/245; 351/244
[58] Field of Search ............. 269/323, 325, 326, 328; 350/571; 351/244, 245, 203; 354/62; 362/804; 378/17, 19, 38, 39, 40, 208, 209; 433/29, 33, 53, 61, 62, 140; 606/4, 5, 6; 128/745

[56] References Cited

U.S. PATENT DOCUMENTS

| | | | |
|---|---|---|---|
| 2,508,449 | 5/1950 | Davis, Jr. et al. | 378/209 |
| 3,201,795 | 8/1965 | Cuppers et al. | |
| 3,544,220 | 12/1970 | Kaye | |
| 3,783,863 | 1/1974 | Kliever | 378/209 |
| 4,071,231 | 1/1978 | Kok | 378/208 |
| 4,643,547 | 2/1987 | Collins et al. | 351/245 |
| 4,665,913 | 5/1987 | L'Esperance, Jr. | |
| 4,770,172 | 9/1988 | L'Esperance, Jr. | |
| 4,779,858 | 10/1988 | Saussereau | 378/209 |

*Primary Examiner*—Rodney B. Bovernick
*Attorney, Agent, or Firm*—Griffin Branigan & Butler

[57] ABSTRACT

The apparatus of this invention is intended for observation and treatment of a patient, in particular for ophthalmological cases. Such apparatus includes an arrangement (10) for ophthalmological observation and treatment, means (12) for effecting positioning and adjustment of said arrangement (10), an underframe (14) for supporting the means (12) and said arrangement (10) as well as a head rest system (16). In this apparatus the means (12) comprises jointed means permitting rotation of the arrangement (10) around a horizontal axis. The apparatus is applied for observing and treating the eyes of a patient who may be seated or recumbent.

11 Claims, 5 Drawing Sheets

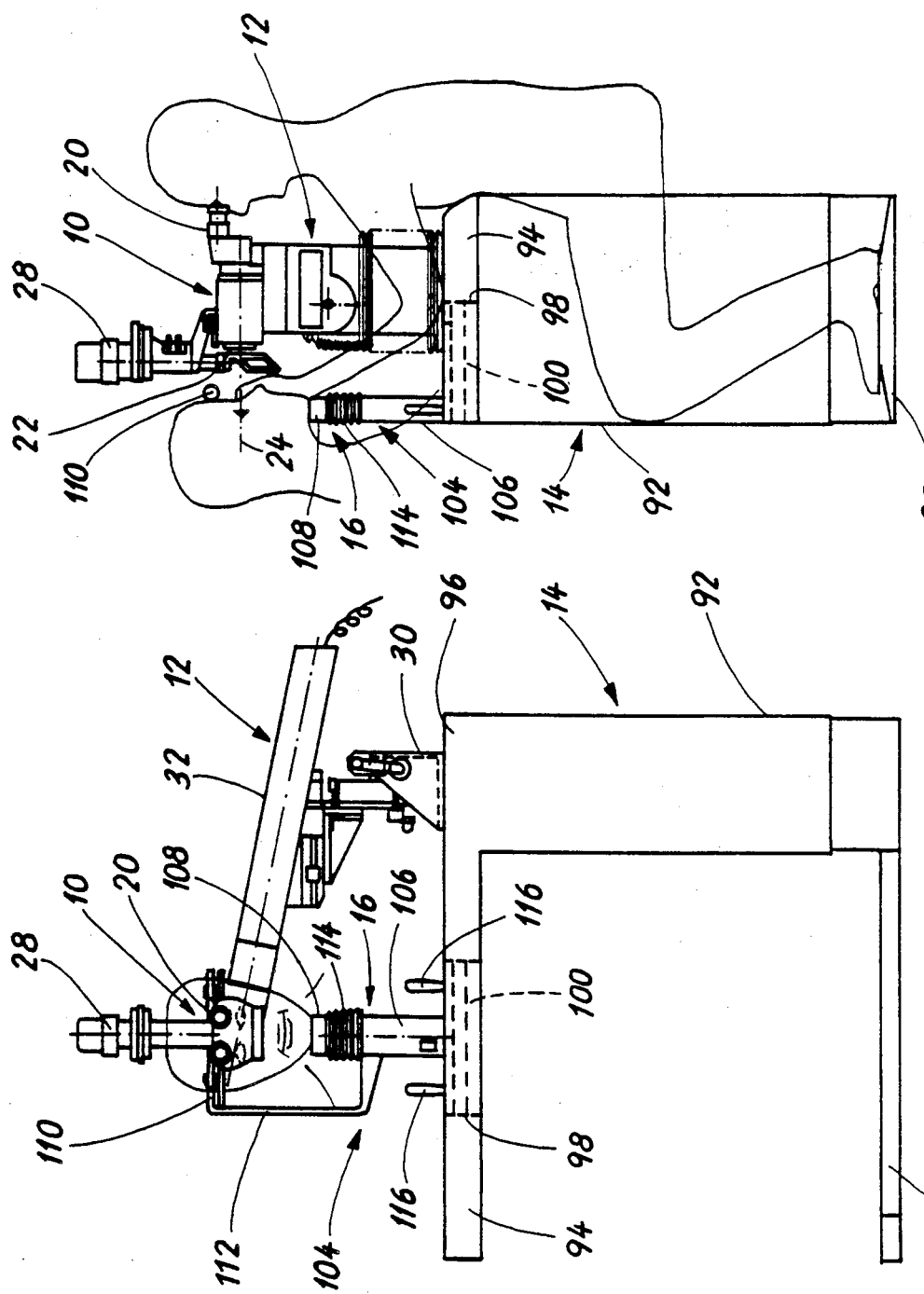

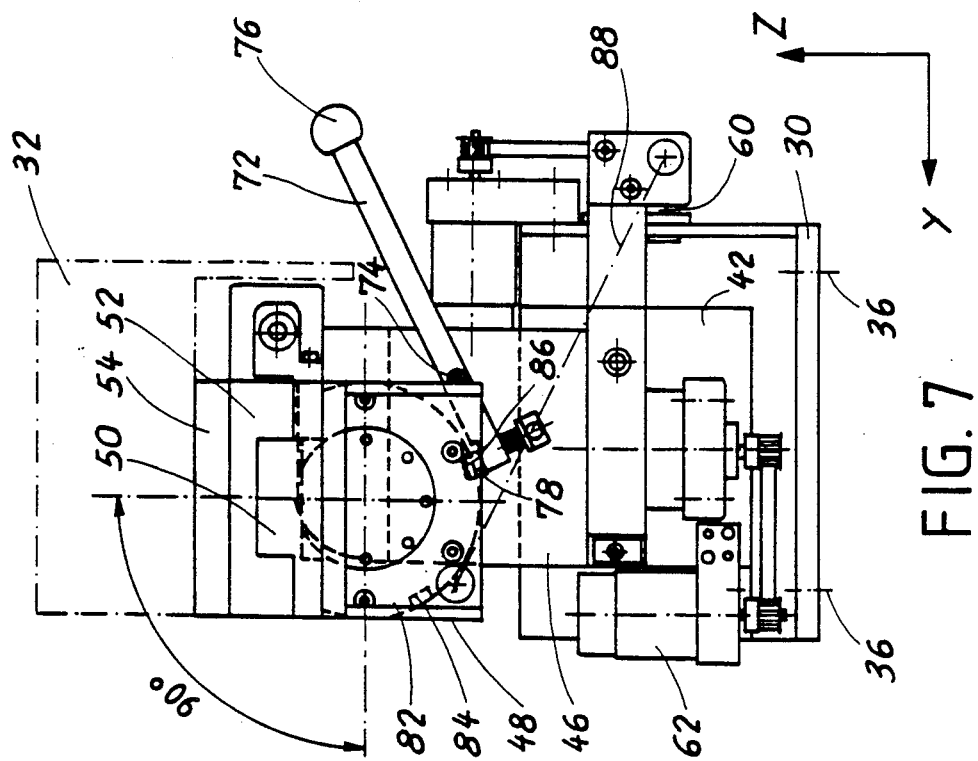
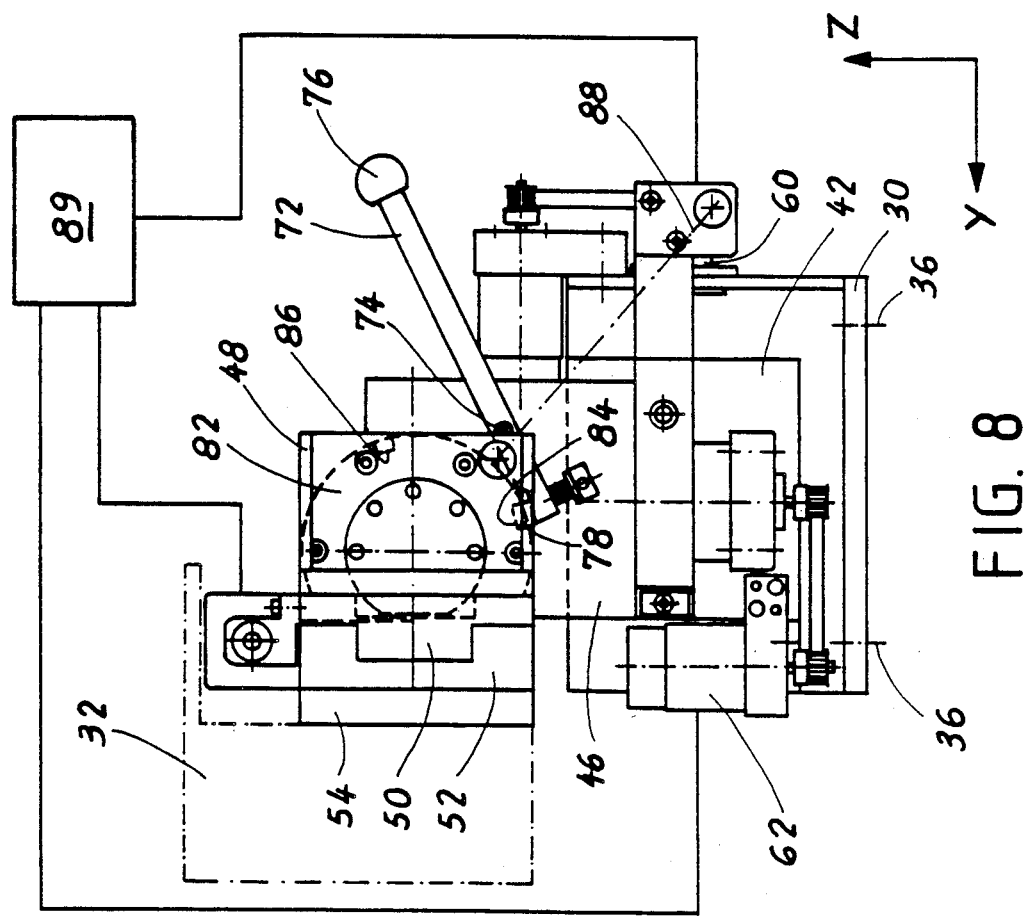

APPARATUS FOR OBSERVATION AND/OR TREATMENT OF A SEATED OR RECUMBENT PATIENT

This invention relates to the medical domain. In particular, the invention concerns an apparatus for the observation and/or treatment of an eye of a patient:

BACKGROUND OF THE INVENTION

Since the introduction and development of ophthalmological surgery, the types of apparatus employed have never ceased to progress in precision and performance (in particular thanks to laser applications).

Nevertheless, up to the present time, it has been impossible to employ the same apparatus for effecting examination and/or treatment of patients which are seated and of recumbent patients.

Such a difficulty obliges the medical team either to invest in specific apparatus for each position or to work only under certain limited conditions (difficulties in treating anaesthetized patients in a seated position by way of example).

In any event, such a lack has aggravated the charges of the medical team or limited its activities.

This invention has as a purpose to overcome such lack by proposing an apparatus for carrying out ophthalmological surgery by laser.

SUMMARY OF THE INVENTION

To this end, the apparatus in accordance with the invention for observing and treating a patient includes an observing and treating arrangement defining an optical output axis, means for effecting positioning and adjustment of said arrangement, an underframe for supporting said means and said arrangement, and a head rest system for immobilizing and positioning the head of the patient, wherein said means comprises a support rigidly mounted on the underframe, an armature integral with said arrangement and a link which couples said support and said armature arranged to permit rotation of the armature around a horizontal axis in order to effect an angular orientation of said optical axis in two directions so as to permit observation and/or treatment of a patient in a seated and recumbent position respectively.

Thanks to these essential characteristics, the apparatus in accordance with the invention enables caring for patients regardless of whether they are in a seated or recumbent position.

Furthermore, as will appear in the description to follow, the practitioner has no need to change either the place or position in which he cares for the patient, seated or recumbent. He may rest seated at the same place whatever be the position of the patient.

Other characteristics and advantages of the apparatus in accordance with this invention will appear from the reading of the following detailed description given by way of non-limiting example and by referring to the attached drawings.

BRIEF DESCRIPTION OF THE DRAWINGS

FIG. 1 is a schematic representation of an apparatus according to the invention seen in profile employed on a patient placed in a seated position;

FIG. 2 is a schematic representation of the same apparatus seen from a facing view under the same conditions of use;

FIG. 7 is a schematic representation of a portion of the support means when the apparatus is employed on a seated patient;

FIG. 8 is a schematic representation of the same support means when the apparatus is employed on a stretched out patient;

DESCRIPTION OF THE PREFERRED EMBODIMENT

Figure 3:
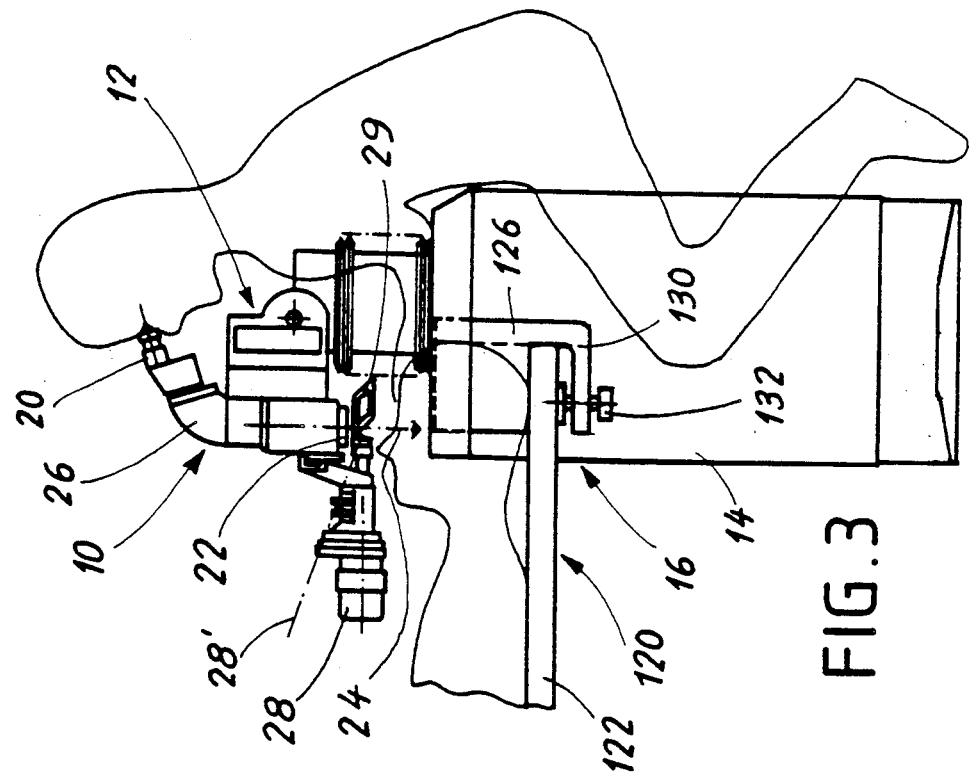
FIG. 3 is a schematic representation of the same apparatus seen in profile and employed on a patient in a stretched out position.

FIGS. 1 and 2 show a profile view and a facing view respectively of the apparatus in accordance with the invention. It is here used on a seated patient. This apparatus includes an arrangement for observation and treatment 10, means 12 for assuring positioning and adjustment of the arrangement 10, an underframe 14 for supporting the arrangement 10 and means 12 as well as head rest system 16 for immobilizing and positioning the head of the patient.

The arrangement for observation and treatment is more particularly intended for eye care. It includes a binocular 20 and a lens 22 together defining an optical system for the observation of the patient by the medical practitioner. This optical system includes furthermore lenses, mirrors and/or prisms and focussing means not shown on the drawing. The optical system defines an optical output axis 24.

The arrangement 10 further includes illumination means for the eye formed by a slit lamp 28, a mirror 29 and lasers (not shown) for treatment and for observation of the eye of the patient.

The slit lamp is of an elongated form located between the practitioner and the patient perpendicular to the optical axis 24 and above the latter when the arrangement is adapted for the examination of a seated patient. Placed thus, the lamp does not hinder the practitioner in his work.

As a variant, lamp 28 may be slightly inclined as schematically shown by the dot-dashed line 28' visible on FIG. 3 in a manner to distance it from the patient. The lamp is movable and may for instance turn on a rail in the form of an arc of a circle (not shown), the concavity of which is on the side of the patient. It includes blocking means (not shown) in order to avoid untimely displacement when the apparatus is arranged so as to treat a patient in the recumbent position.

The means 12, the underframe and the head rest system will be described subsequently in detail. On FIGS. 1 and 2 one may already note that the apparatus enables observation and treatment of a patient in a seated position. To this end the patient has his head immobilized on the head rest system, one eye aligned on the output axis 24 of the arrangement 10. The alignment of the axis and of the eye is brought about by the medical practitioner by means of control means not shown on these figures.

The practitioner, seated facing the patient, observes the eye of the latter through a binocular 20 in order to diagnose the problem, and as well to activate the laser or lasers when a treatment must be effected.

Figure 4:
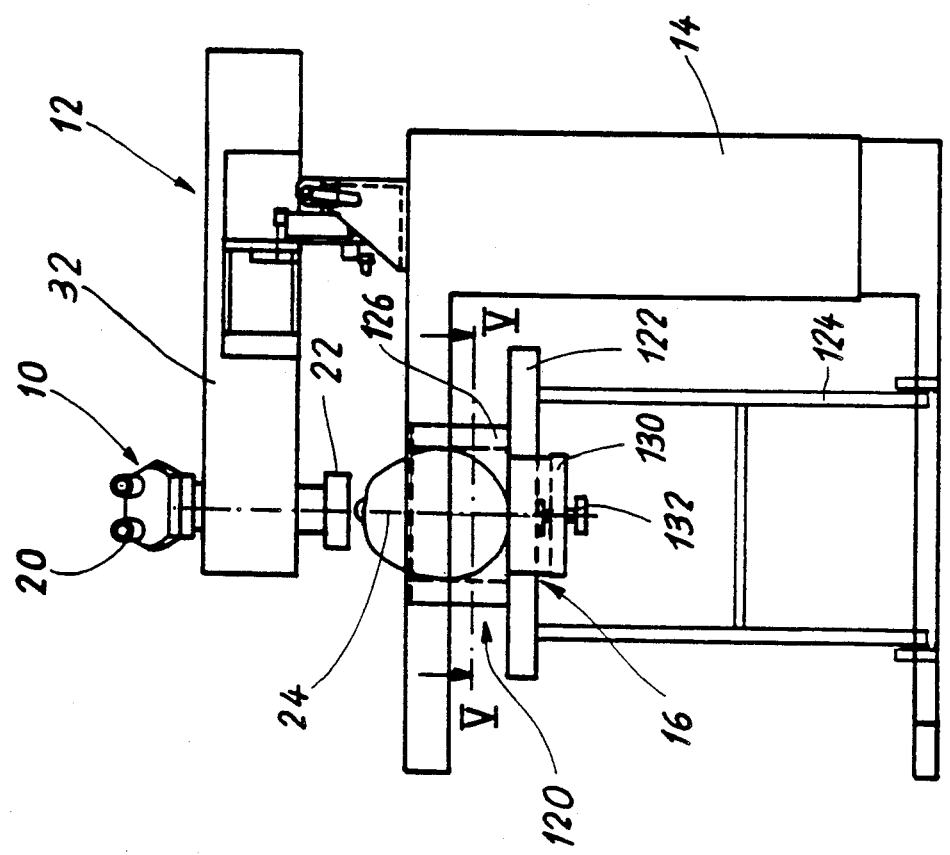
FIG. 4 is a representation of the same apparatus seen from a facing position in the same conditions of use as those of FIG. 3.

We will now refer to FIGS. 3 and 4 which represent the same apparatus arranged this time in order to permit observation and treatment of the eye of a patient in recumbent position.

On these figures there will be found the observation and treatment arrangement 10, the means 12 for assuring positioning and adjustment of the arrangement 10, the underframe 14 for supporting the arrangement 10 and means 12 as well as the head rest system 16 for immobilizing and positioning the head of the patient. One may also see binocular 20, lens 22 defining the output axis 24 as well as the illuminating means 28 for the eye.

The optical system further includes an elbow 26 comprising a prism not shown on the drawing. The elbow is removable, for instance it may be fastened by means of a bayonet attachment.

With the apparatus which has just been described, the patient is recumbent and the optical axis 24 is vertical. The practitioner is seated and observes the eye of the patient through binocular 20. Thanks to the presence of elbow 26, the practitioner may rest seated in order to observe and treat the patient, the binocular 20 in effect forming a small angle with the horizontal plane.

Figure 9:
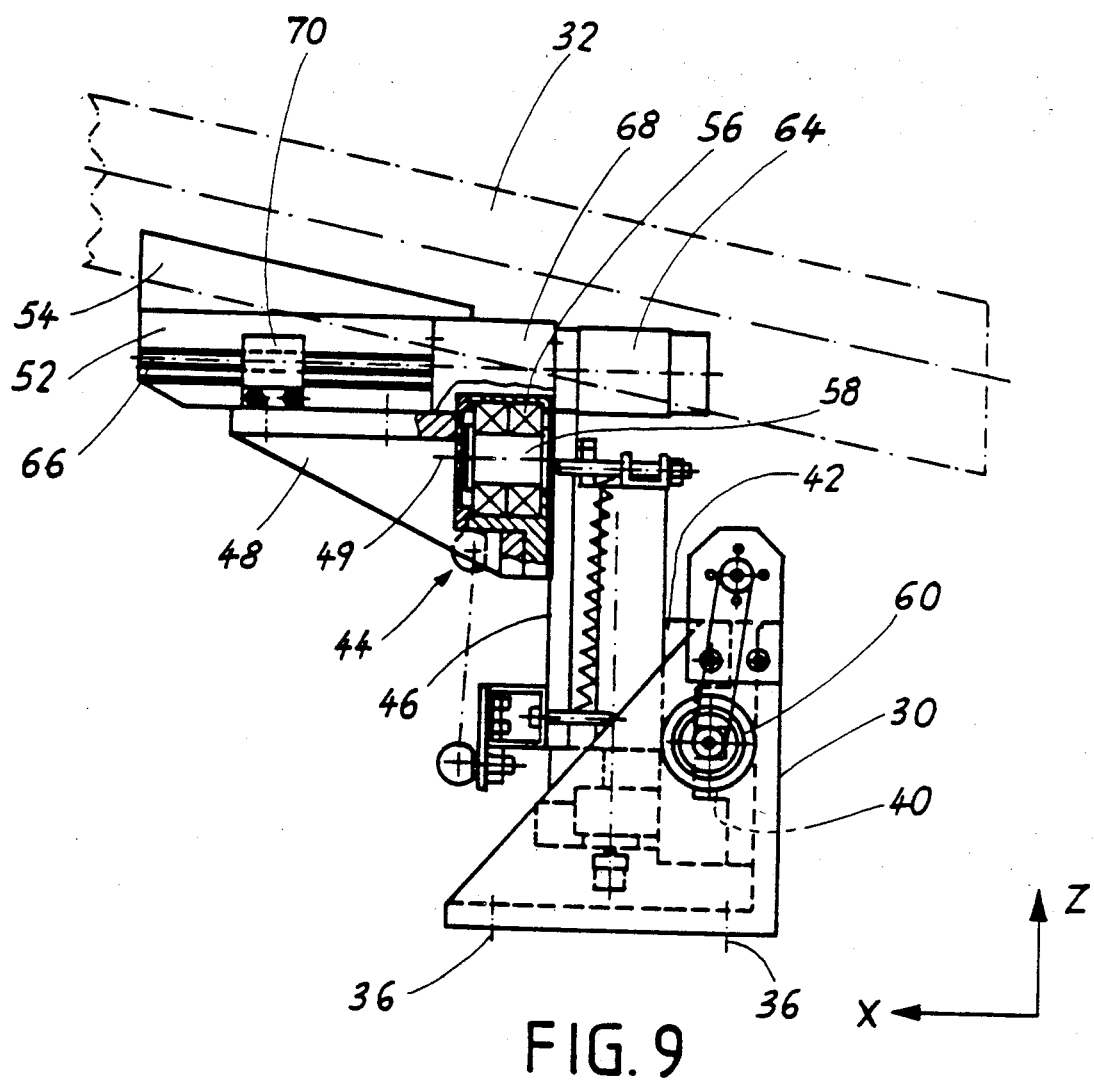
FIG. 9 is a schematic representation of the same support means seen from the face view when the apparatus is employed on a seated patient.

We will now describe in greater detail the means 12 shown on FIGS. 7 to 9. It includes an element support 30 fixed to the underframe 14, an armature 32 as well as means for connecting the armature 32 to the support 30 which permit positioning and displacing the armature 32 and thereby the arrangement 10.

More precisely, support 30 is fixed to the underframe by means of screws schematically represented at 36.

Figure 6:
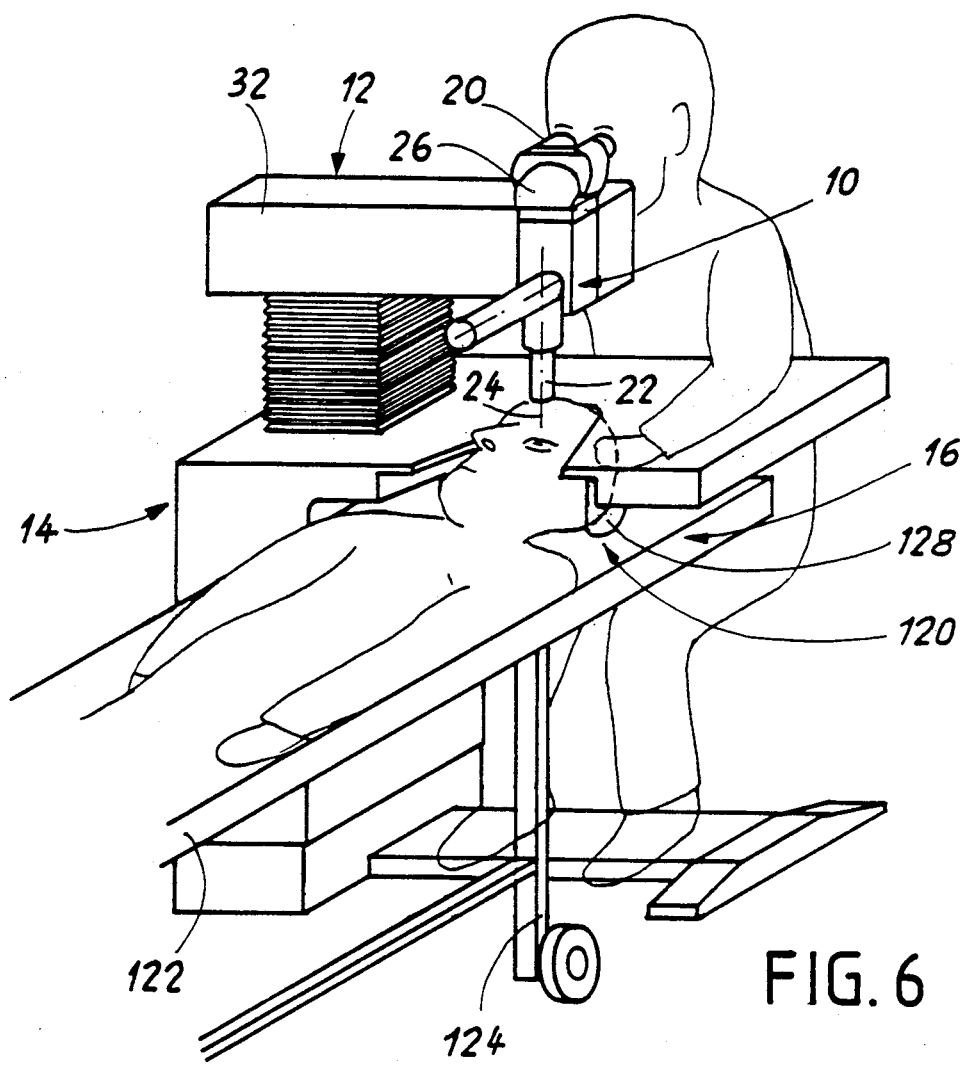
FIG. 6 is a schematic representation of a perspective view of the apparatus shown on FIGS. 1 to 4 in conditions of use identical to those of FIG. 3.
Figure 5:
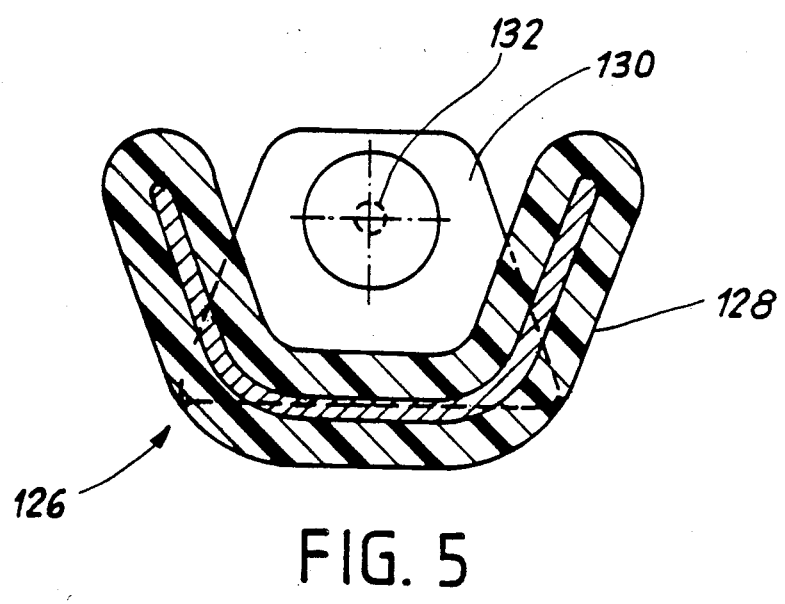
FIG. 5 is a cross-sectional representation of means for immobilizing the head of the patient in a stretched out position.

Thus, as one may more particularly see on FIGS. 2, 4 and 6, armature 32 is formed of a tube bearing the arrangement 10 at one of its extremities. This tube is placed substantially horizontally between the patient and the practitioner and is progressively reduced from the support towards the arrangement. The interior of the tube is advantageously employed in order to house various elements associated with the arrangement 10, for example a laser or lasers or indeed optical fibres, electrical wires, etc. connecting to said arrangement the heavy apparatus arranged in the underframe 14 or beside the latter.

The coupling means comprise more particularly a first part to permit displacement of the arrangement 10 according to four degrees of freedom, and a second part for controlling the movement and the positioning of the arrangement 10. The first part comprises an assembly of three orthogonal guidance components, each comprising a rail and a slide as well as a bearing assuring rotation about a horizontal axis.

A first rail 40 (FIG. 9) oriented according to the X axis of the frame of reference shown on FIGS. 7 to 9 is fixed to the support 30. This rail 40 cooperates with a carriage 42 including two orthogonal slideways, one of which is engaged on rail 40. This first part further includes a bracket 44 formed by a rail along axis Z engaged in the second slideway of carriage 42, a riser 46 fastened to the rail along axis Z and of a corbel 48 coupled to the riser 46 in a hinged manner and movable in rotation around an axis 49 parallel to axis Y by means which will be described hereinafter.

The corbel 48 bears a rail 50 along axis Y. A slideway 52 engaged with rail 50 bears armature 32 via a plate 54.

The hinging of corbel 48 onto riser 46 is effected by means of a double ball bearing 56, the cages of which are fastened to corbel 48 and in which is engaged a shaft 56 fixed to the riser 46.

In this arrangement the means 12 thus comprises four degrees of freedom, i.e. three in translation and one in rotation, the axis of rotation being horizontal.

The second part of the means intended to control the movement and positioning of the arrangement 10 comprises three assemblies which in principle are identical and each of which drives the armature along one axis. Each assembly includes a motor, an endless screw and nut and a positive non-slip coupling between the motor and the endless screw. More precisely, this second part comprises a motor 60 fixed to support 30. This motor drives carriage 42 via a non-slip positive coupling, in particular by a nut fixed to the latter by an endless screw mounted on the support and by gears or by means of a toothed belt. The gears, the screw and the nut are not visible on the drawing.

A motor 62 fixed to carriage 42 drives the riser 46 along axis Z by means similar to those associated with motor 60.

A motor 64 (FIG. 9) mounted on corbel 48 assures displacement along axis Y. Driving is brought about by means of an endless screw 66 via gearing housed in a case 68. The endless screw 66 cooperates with a nut 70 fixed to plate 54.

Thus, as has been explained hereinabove, the armature may pivot around a horizontal axis. It is evident that ill timed manipulations must be prevented. It is for this reason that it is necessary to foresee means for blocking the armature in its end positions. To this end the means 12 includes a lever 72 (FIG. 7 and 8) which pivots at 74 on riser 46. The lever 72 comprises a handle 76 at one of its ends and a finger 78 at the other end. A spring, not shown on the drawing and of which one end is fastened to riser 46 and the other to lever 72, tends to urge lever 72 and more particularly its finger 78 against a cam 82 fixed to the corbel 48. This cam 82 includes a portion in the form of an arc of a circle which extends over about 90° with notches 84 and 86 at each of its ends. These notches 84 and 86 are arranged in a manner such that finger 78 may engage therein without play.

When the practitioner swings the armature, it is evident that he must above all avoid shocks. It is for this reason that the means 12 includes furthermore a hydraulic brake schematically shown at 88 which guarantees swinging of the armature without shocks.

In order to control positioning of the armature, the practitioner has available a control post schematically shown at 89 (FIG. 8) which enables controlling driving in rotation of motors 60, 62 and 64. This control post is described in detail in a Swiss patent application entitled "Control Arrangement For An Apparatus For Ophthalmological Treatment" in the name of the assignee of the present invention.

We will now describe more fully the underframe 14 by means of reference to FIGS. 1 to 4 and 6.

This underframe includes a base 90, a riser 92 and a table 94. The riser 92 is fixed to one of the base's 90 end. It has substantially the height of a standard work table, i.e. about 80 cm. It may advantageously include means for adjusting this height. Table 94 is fastened to riser 92 as a cantilever above base 90. The part 96 of table 94 located in the elongation of riser 92 bears support 30.

Table 94 includes on the side intended to receive the patient a cut-out 98 of trapezoidal form.

When the apparatus is arranged to permit observation and treatment of a seated patient such as shown on FIGS. 1 and 2, the cut-out 98 is blocked by a piece 100 of complementary form provided with a slider engaged in a slideway formed in the thickness of the table.

Part 100 bears an assembly 104 permitting positioning of the head of a patient in a seated position. This assembly comprises a column 106 fixed to part 100, a chin support 108 at the head of column 106 and a forehead support 110 coupled to column 106 by a head rest bracket 112. The column 106 is furthermore provided with means enabling adjustment of the position of the chin support 108, as a function of the physiognomy of the patient, schematically shown by bellows 114. These means may include a hydraulic piston for instance.

In order to improve the stability of the patient and diminish his fatigue, the assembly 104 is completed by two handles 116 (FIG. 2) likewise fixed to part 100. These handles, when they are held by the patient, encourage a position of the torso and the head guaranteeing good working conditions.

On FIGS. 3 to 6 may be seen an assembly 120 permitting in particular the positioning of the head of a patient in recumbent position. It includes a bed 122 provided with feet 124 mounted on castors and a head block 126. The head block 126, more particularly visible on FIG. 5, includes an upper part 128 in the form of an open U, made from a padded rigid material and a fastening square 130 provided with a blocking screw 132. The head block 126 is arranged in a manner to be rigidly fastened onto bed 122. Its upper part 128 exhibits an outer form complementary to that of the cut-out 98. Furthermore, the opening of the U is dimensioned such that the head of the patient may be immobilized and positioned.

In this manner, in order to treat a patient in recumbent position, the head block 126 is initially fastened to table 122. The patient is then installed with his head being positioned and immobilized in the head block 126. Bed 122 is then installed by engaging the head block 126 in the cut-out 98. Thus, the head of the patient is protected during the installation and is already pre-positioned. There is thus nothing further for the practitioner to do than to adjust the position of the arrangement 10 thanks to the control means and to adapt the arrangement to the special physiognomy of the patient in order to observe and treat one or the other of his eyes.

Thus, as has just been explained, such an apparatus permits observation and treating of a patient whether in seated or recumbent position and this for a very small increase in the cost of the apparatus.

The apparatus such as described may include various improvements. Thus, all or part of the means 12 may advantageously be protected by a bellows as may be seen on FIGS. 1, 3 and 6.

The control arrangement 89 such as provided includes a set of keys, each key being associated with one of the motors of the means 12. As a variant, it would likewise be possible to provide a position detector for the armature, permitting a control means to know whether the apparatus is in working position with a patient seated or recumbent. In this case a control member could be associated with the control for displacing the arrangement in the direction of the eye of the patient. For the patient in seated position, this control member would be associated with the motor 60 working on axis X while in recumbent position it would be associated with the motor 64 working on axis Z. Second control member would be associated with the displacement control for the arrangement in a direction perpendicular to the axis running between the two eyes. With the patient in seated position, this member would be associated with the motor working on axis Z and in recumbent position with the motor working on axis X. In this manner, the practitioner would have available a control arrangement the behaviour of which in respect of the patient would be the same whether the latter was recumbent or seated.

The special arrangement of the various lasers included in the apparatus according to the invention is described in the Swiss patent application entitled "Arrangement For Surgical Treatment Of A Point Situated In An Eye" filed by the assignee at the same time as the present application. It will thus not be described in detail herein.

It will nevertheless be noted that certain power lasers may not be employed with the apparatus since they release too much heat.

To couple power lasers to the arrangement, one may employ optical fibres, not shown on the drawing.

A first fibre is fixed to the laser and a second to the arrangement, the two fibres being coupled to one another by a two-part connector, one part being fastened to the end of the armature 32 adjacent the support and the other to the free end of the first fibre.

Thanks to this particular arrangement, the coupling between the power laser or lasers and the arrangement is assured notwithstanding that it passes via a movable armature.

What we claim is:

1. An apparatus for observing and treating a patient which includes:
    an observing and treating arrangement defining an optical output axis, said arrangement being adapted for the observation and treatment of an eye of the patient,
    means for effecting positioning and adjustment of said arrangement,
    an underframe for supporting said means and said arrangement, and
    a head rest system for immobilizing and positioning the head of the patient,
    wherein said means comprises a support rigidly mounted on the underframe, an armature integral with said arrangement and a link which couples said support and said armature arranged to permit rotation of the armature around a horizontal axis in order to ensure an angular orientation of said optical axis in two directions so as to permit observation and/or treatment of a patient in a seated and recumbent position respectively.

2. An apparatus as set forth in claim 1 wherein said means further includes an assembly of rails and slideways cooperating two by two thereby to enable displacement of the armature relative to the underframe in three orthogonal directions.

3. An apparatus as set forth in claim 1 wherein said armature includes a cantilevered arm fastened to the underframe through said means and bearing said arrangement at its free end.

4. An apparatus as set forth in claim 1 wherein said head rest system includes a first assembly adapted to be detachably fastened to the underframe in order to immobilize and position the head of a seated patient and a second assembly associated with a bed intended for a recumbent patient so as to immobilize and position the head thereof.

5. An apparatus as set forth in claim 4 wherein the underframe comprises a table provided with a cutout and a removable piece of complementary form accommodated and positioned in the cutout and bearing said first assembly.

6. An apparatus as set forth in claim 4 wherein the second assembly includes a positioning block defining a cavity adapted to the form of the patient's head so as to maintain the latter in a fixed position relative to the underframe when the apparatus is adapted for observation and treatment of a recumbent patient.

7. An apparatus as set forth in claim 6 wherein the outer form of said block is complementary to that of said cutout whereby it may be accommodated and positioned in said cutout.

8. An apparatus as set forth in claim 1 wherein said arrangement includes a lens located proximate the eye of the patient, an eyepiece for enabling observation of the eye of the patient by a medical practitioner and means for deviating the observation beam whereby the practitioner may be seated when observing and treating a recumbent patient.

9. An apparatus as set forth in claim 2 wherein said armature includes a cantilevered arm fastened to the underframe through said means and bearing said arrangement at its free end.

10. An apparatus as set forth in claim 5 wherein the second assembly includes a positioning block defining a cavity adapted to the form of the patient's head so as to maintain the latter in a fixed position relative to the underframe when the apparatus is adapted for observation and treatment of a recumbent patient.

11. An apparatus as set forth in claim 10 wherein the outer form of said block is complementary to that of said cutout whereby it may be accommodated and positioned in said cutout.

* * * * *